United States Patent [19]

Umezawa et al.

[11] 4,156,078

[45] May 22, 1979

[54] PROCESS FOR THE SYNTHESIS OF 3',4'-DIDEOXYKANAMYCIN B AND PRODUCTS

[75] Inventors: Hamao Umezawa; Sumio Umezawa, both of Tokyo; Tsutomu Tsuchiya, Yokohama, all of Japan

[73] Assignee: Zaidan Hojin Biseibutsu Kagaku Kenkyu Kai, Tokyo, Japan

[21] Appl. No.: 745,015

[22] Filed: Nov. 26, 1976

[30] Foreign Application Priority Data

Dec. 11, 1975 [JP] Japan .................................. 50-146903

[51] Int. Cl.$^2$ ............................................ C07H 15/22
[52] U.S. Cl. ...................................... 536/10; 424/180; 536/17 R
[58] Field of Search ..................................... 536/10, 17

[56] References Cited

U.S. PATENT DOCUMENTS

| Re. 28,647 | 12/1975 | Umezawa et al. | 536/10 |
|---|---|---|---|
| 3,868,360 | 2/1975 | Daniels et al. | 536/17 |
| 3,929,762 | 12/1975 | Umezawa et al. | 536/10 |

FOREIGN PATENT DOCUMENTS 1349302  4/1974  United Kingdom ...................... 536/10

OTHER PUBLICATIONS

Jikihara et al. Bulletin of the Chem. Soc. of Japan, vol. 46, pp. 3507-3510, 1973.
Umezawa et al., "Jour. of Antibiotics", vol. XXIV, No. 7, 1971, pp. 485-487.
Umezawa et al., "Jour. of Antibiotics", vol. XXV, No. 12, 1972, pp. 743-745.
Umezawa et al., "Bulletin of the Chem. Soc. of Japan", vol. 45, pp. 3624-3628, 1972.

*Primary Examiner*—Johnnie R. Brown
*Attorney, Agent, or Firm*—Herbert W. Taylor, Jr.

[57] ABSTRACT

A useful antibiotic, 3',4'-dideoxykanamycin B can be prepared in shortened steps and in an improved overall yield by a new process starting from kanamycin B via new intermediate derivatives of kanamycin B in which all the amino groups and possibly the 2"-hydroxyl group are protected with sulfonyl-type protecting groups selected from lower alkyl-, aryl- and aralkyl-sulfonyl groups.

20 Claims, No Drawings

PROCESS FOR THE SYNTHESIS OF 3',4'-DIDEOXYKANAMYCIN B AND PRODUCTS

BACKGROUND OF THE INVENTION

This invention relates to a new process for the synthesis of 3',4'-dideoxykanamycin B.

DESCRIPTION OF THE PRIOR ART

3',4'-Dideoxykanamycin B is a semisynthetic antibiotic having a high antibacterial activity against drug-resistant bacteria and hence it is widely used in clinical applications (British Pat. No. 1,349,302 and "Journal of Antibiotics" Vol. 24 (1971), p. 485).

3',4'-Dideoxykanamycin B has the following structural formula:

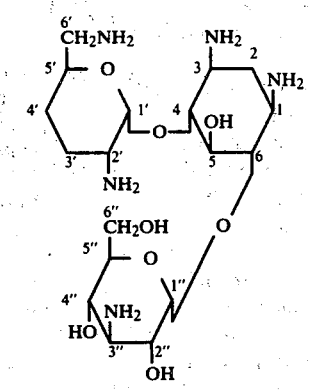

Known method of preparing 3',4'-dideoxykanamycin B, which may be hereinafter referred to as DKB, includes the following two procedures:

(1) Starting from kanamycin B, this is reacted with an alkoxycarbonyl halide to protect the five amino groups of the kanamycin B and then the hydroxyl groups at the 3'-, 4'-, 4"- and 6"-positions are protected by the conversion of a pair of the 3'- and 4'-hydroxyl groups as well as a pair of the 4"- and 6"-hydroxyl groups into the form of acetal or ketal. The 2"-hydroxyl group is then protected with an alkanoyl or aroyl group and the protecting group for the 3'- and 4'-hydroxyl groups is selectively removed by treatment with a dilute acid, whereupon the sulfonylation of the 3'- and 4'-hydroxyl groups, the formation of a double bond between the 3'- and 4'-carbon atoms by treatment with an alkali metal bromide or iodide and zinc powder and the hydrogenation of the double bond are successively performed. Thereafter, the protecting groups for the 4"- and 6"-hydroxyl groups is removed by treatment with an acid and finally the remaining protecting groups are removed to produce DKB (see British Pat. No. 1,349,302).

(2) The amino groups of kanamycin B as starting material are protected by conversion into a group of Schiff-base type, and a pair of the 3'- and 4'-hydroxyl groups as well as a pair of the 4"- and 6"-hydroxyl groups are protected by the conversion into the form of acetal or ketal. The protected derivative so obtained is subjected to the successive treatments as just mentioned above to produce DKB (see the above-mentioned British Patent).

This known method needs intricate steps of protecting the amino and hydroxyl groups and removing the protecting groups and give DKB only in a poor overall yield as low as 10%.

SUMMARY OF THE INVENTION

An object of this invention is to provide a new process for the synthesis of DKB which is free from the above drawbacks of the knwon method. The other object of this invention is to provide a new improved process of synthetising DKB from kanamycin B which is operable with a reduced number of the reaction steps and able to give DKB in an improved overall yield. Another objects will be clear from the following descriptions.

As a result of our further studies, we have now found that the five amino groups of kanamycin B may also be protected by an amino-protective group of alkylsulfonyl, arylsulfonyl or aralkylsulfonyl type by reacting kanamycin B with an alkylsulfonic, arylsulfonic or aralkylsulfonic halide in an organic solvent, either aqueous or anhydrous, such as aqueous dioxane, aqueous acetone in the presence of a base, for example, an alkali such as sodium carbonate. We have further found that the pair of the 4"- and 6"-hydroxyl groups of the penta-N-sulfonylated kanamycin B so obtained may selectively protected by reacting with an alkylidenating, arylidenating, cyclohexylidenating or tetrahydropyranylidenating agent which is known to introduce a di-valent hydroxyl-protecting radical as described in British Pat. No. 1,349,302, at a relatively low temperature of eg. 10°–80° C., without blocking the pair of the 3'- and 4'-hydroxyl groups. The resulting 4", 6"-O-protected derivative of the penta-N-sulfonylated kanamycin B can be converted into the corresponding 3',4'-di-O-alkyl-, aryl- or aralkylsulfonylated derivative, possibly together with the corresponding 3',4',2"-tri-O-alkyl-, aryl- or aralkylsulfonylated derivative, when said 4",6"-O-protected derivative is reacted with alkyl-, aryl- or aralkylsulfonic chloride in a solvent such as pyridine at a low temperature of eg. −30° C. to 30° C. When the 3',4'-di-O-alkyl, aryl- or aralkylsulfonylated derivative or the 3',4',2"-tri-O-alkyl-, aryl- or aralkylsulfonylated derivative is treated with a metal iodide such as sodium iodide or lithium iodide in an organic solvent such as N,N-dimethylformamide at a temperature of eg. 50°–150° C., the 3'- and 4'-alkyl-, aryl- or aralkylsulfonyloxy groups are removed to give the corresponding 3',4'-unsaturated derivative (that is, the corresponding 3'-eno derivative). When the latter is hydrogenated, it is converted into the corresponding 3',4'-saturated derivative, that is, the 3',4'-dideoxykanamycin B of which the five amino groups and possibly the 2"-hydroxyl group still remain sulfonylated and of which the pair of the 4"- and 6"-hydroxyl groups still remain protected by the di-valent hydroxyl-protecting radical. This 3',4'-dideoxykanamycin B derivative may be converted into the corresponding penta-N-sulfonylated and possibly 2"-O-sulfonylated DKB derivative, by treating with a dilute acid to remove therefrom the protective group for the 4"- and 6"-hydroxyl groups.

Thus, we have now succeeded in preparing the protected derivatives of 3',4'-dideoxykanamycin B in which the five amino groups of the 3',4'-dideoxykanamycin B molecule are protected with a protective group selected from lower alkyl-, aryl- and aralkylsulfonyl groups and optionally the 2"-hydroxyl group is also protected with one selected from these groups. We have also found that the amino-protective radicals of the aforesaid sulfonyl type and the possible 2"-hydroxyl-protective group of the aforesaid sulfonyl type can be removed at once by treating the abovementioned protected derivatives with an alkali or alkaline earth metal in ammonia or an alkylamine or a mixture thereof.

DESCRIPTION OF THE INVENTION

According to a first aspect of this invention, therefore, there is provided a process for the preparation of 3',4'-dideoxykanamycin B of the formula (I):

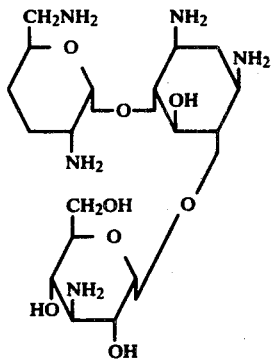

which comprises interacting a compound of the formula (II):

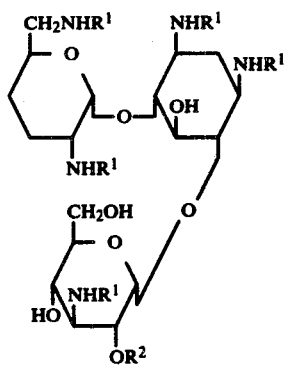

wherein each $R^1$ represents an amino-protecting group of a type selected from lower alkyl-sulfonyl, aryl-sulfonyl and aralkyl-sulfonyl groups and $R^2$ represents hydrogen atom or a hydroxyl-protecting group of a type selected from lower alkyl-sulfonyl, aryl-sulfonyl and aralkyl-sulfonyl group, with an alkali or alkaline earth metal in ammonia or a lower alkylamine or a mixture thereof to remove therefrom the protecting groups $R^1$ and $R^2$.

Examples of the protecting radicals $R^1$ and $R^2$ in the above formula (II) include lower alkyl-sulfonyl group, for example, methyl-, ethyl-, propyl-, isopropyl- and butyl-sulfonyl; aryl-sulfonyl group, for example, p-toluene-, O-nitrobenzene-, p-nitrobenzene-, p-methoxybenzene- and 1- or 2-naphthalene-sulfonyl; and aralkyl-sulfonyl group, for example, benzylsulfonyl. Preferred protecting radicals $R^1$ and $R^2$ include methylsulfonyl, tosyl and benzylsulfonyl group.

The first aspect process of the invention is carried out using an alkali metal selected from lithium, sodium and potassium or an alkaline earth metal selected from calcium, magnesium and barium or a mixture thereof, in ammonia, a lower alkylamine or a mixture thereof. It is convenient to use lithium or sodium. The lower alkylamine includes mono-, di- and tri- lower alkyl amines, for example, methyl-, ethyl- or propyl-amine, dimethyl- or diethyl-amine and trimethyl- or triethyl-amine; aromatic amines, for example, aniline, lower alkyl aniline such as methyl-dimethyl-, ethyl- and diethyl-aniline, toluidine, benzylamine, dibenzylamine, diphenylamine and naphthylamine; and mixtures thereof. It is preferred to use liquid ammonia, methylamine or ethylamine or a mixture thereof. The reaction may be, if desired, carried out in the presence of an organic solvent, for example, methanol, ether and benzene.

A temperature at which the reaction is carried out may be in the range from $-80°$ C. to $+50°$ C. When the reaction is carried out at room temperature or higher, it is preferably effected in a sealed tube. Suitably, the reaction is continued for 0.5 to 24 hours.

An amount of the alkali or alkaline earth metal to be used is suitably about 10 to 100 moles per mole of the compound of the above formula (I). The metal may be added in two or several portions and in the form of divided pieces.

After the reaction is completed, ammonium chloride or an equivalent is added to the reaction mixture to collapse the residual alkali or alkaline earth metal, then the solvent removed and the residue taken up in water. The resultant product may be purified by a conventional technique, for example, by column chromatography to give the desired compound, 3',4'-dideoxykanamycin B. The treatment of this compound with an acid in a usual manner may yield its acid addition salt including sulfate, hydrochloride and methanesulfonate.

We have also found that when the 3',4'-unsaturated derivative corresponding to the compound of the formula (II) is treated with an alkali or alkaline earth metal in the same manner as above, the protecting groups $R^1$ and $R^2$ can be concurrently removed and that the product free from the protecting groups and having a double bond between the 3'- and the 4'-positions can be subjected to hydrogenation to produce DKB.

According to a second aspect of this invention, therefore, there is provided a process for the preparation of 3',4'-dideoxykanamycin B of the above formula (I), which comprises interacting a compound of the formula (III):

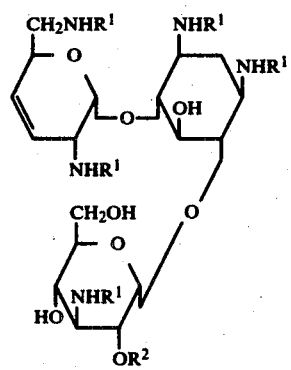

wherein each $R^1$ represents an amino-protecting group of a type selected from lower alkyl-sulfonyl, aryl-sulfonyl and aralkyl-sulfonyl groups and $R^2$ represents hydrogen atom or a hydroxyl-protecting group of a type selected from lower alkyl-sulfonyl, aryl-sulfonyl and aralkyl-sulfonyl groups, with an alkali or alkaline earth metal in ammonia or a lower alkylamine or a mixture thereof to remove therefrom the protecting groups $R^1$ and R$^2$, thereby producing 3',4'-dideoxy-3'-enokanamycin B of the formula (IV):

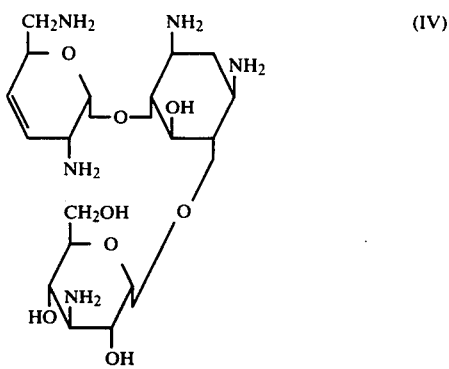

and subjecting the compound (IV) to hydrogenation.

The first stage of this second aspect process can be carried out under the same conditions and in the same manner as mentioned hereinbefore for the process according to the first aspect of this invention.

The second stage consists in hydrogenation reduction of 3',4'-dideoxy-3'-enokanamycin B produced in the first stage. The reduction may be performed with addition of hydrogen gas in a suitable solvent in the presence of a conventional hydrogenation catalyst, for example, Ranney nickel, platinum, platinum oxide, palladium-carbon, cobalt, rhodium complex, copper and iron. Examples of the solvent to be used include water, methanol, ethanol, isopropanol, acetone, dioxane, pyridine, tetrahydrofuran, dimethylformamide, cyclohexane, ethyl acetate and mixtures thereof.

The reduction may be carried out at a temperature from $-40°$ C. to $+120°$ C., although a preferred range is from ambient temperature to 100° C. Whilst the reduction may readily proceed under atmospheric pressure, it may also be effected under a pressure of 5 to 100 Kg/cm$^2$. The reaction time is suitably 0.5 to 48 hours.

3',4'-dideoxykanamycin B obtained in this manner can be purified as already stated and converted to its acid addition salts, for example, sulfate, hydrochloride, methanesulfonate and the like.

This invention provides a new course for synthesis of 3',4'-dideoxykanamycin B from kanamycin B in good yields and this course has the following great advantages:

(1) The respective steps of which the new course consists are simplified and the overall yield of DKB may reach 40% or more on the basis of the initial material kanamycin B.

(2) The step of protecting the 2"-hydroxyl group with, for example, an acyl group can be omitted, leading to the reduction in number of steps;

(3) The removal of the protecting radicals for the amino and the hydroxyl groups can be performed at a time and no side reactions occur;

(4) The process can avoid the use of zinc which has hitherto been required to form the double bond between the 3'- and 4'-positions, resulting in reduction in cost and elimination of disposal problem.

The compounds of the formula (II) in which the amino and optionally the 2"-hydroxyl groups are protected with sulfonyl-type protecting radicals may be made by the following procedure:

Kanamycin B (free base) is reacted with a substantially stoichiometric quantity of a sulfonic halide of the formula:

$$R^3SO_2X$$

wherein R$^3$SO$_2$- has the same meaning as R$^1$ and X is halogen atom such as chlorine or bromine atom, to produce the penta-N-sulfonylated kanamycin B. This reaction can be carried out in a suitable organic solvent such as aqueous dioxane or aqueous acetone at a temperature of e.g. from $-30°$ C. to $+50°$ C. in the presence of a base, preferably an alkali such as sodium carbonate.

The sulfonylated product is then interacted with an alkylidenating, arylidenating, cyclohexylidenating or tetrahydropyranylidenating agent at a relatively low temperature, for example, at 10° to 80° C. so as to protect selectively the 4"- and 6"-hydroxyl groups with such a protecting group of acetal or ketal type which is as described in British Pat. No. 1,349,302. There is thus produced the 4",6"-O-protected, penta-N-sulfonylated derivative of kanamycin B in which the 4"- and 6"-hydroxyl groups are protected with an alkylidene, arylidene, cyclohexylidene or tetrahydropyranylidene group.

Thereafter, the 4",6"-O-protected, penta-N-sulfonylated derivative is again reacted with a sulfonic halide of the formula: R$^3$SO$_2$X wherein R$^3$ and X are as defined above and which may be the same as or different from that use for the first sulfonylation. A preferred sulfonic halide is benzylsulfonyl chloride. The reaction is carried out in a suitable solvent, preferably pyridine at a low temperature, for example, $-30°$ to $+30°$ C. Thus, the 3'- and 4'-hydroxyl groups and possibly the 2"-hydroxyl group are protected to give the 3',4'-di-O-sulfonylated product or the 3',4',2"-tri-O-sulfonylated product or a mixture thereof.

The product is then treated with a metal bromide or iodide, preferably sodium iodide in a suitable organic solvent such as N,N-dimethylformamide at a temperature, for example, from 50° to 150° C. for a period, generally of 15 minutes to 3 hours, so that the 3'- and 4'-sulfonyloxy groups are removed, giving the 3',4'-unsaturated derivative (the 3'-eno derivative). Thus, the 3',4'-unsaturated derivative is produced, which is then subjected to a reduction, preferably a catalytic hydrogenation by any known method, for example, by a method described in British Pat. No. 1,349,302 or Japanese Patent Publication No. 7595/75 to give the corresponding penta-N-sulfonyl-4",6"-O-protected-3',4'-dideoxykanamycin B. In order to remove the 4",6"-O-protecting group from the product, the latter is treated by a known technique which depends upon the nature of the 4",6"-O-protecting group, resulting in the production of the compound having the above formula (II).

The compounds of the above formula (III) may be made by subjecting the 3',4'-unsaturated derivative prepared as mentioned above directly to the treatment for removal of the 3',4'-O-protecting groups as already stated.

For the whole synthesis of DKB from kanamycin B, therefore, the third aspect of this invention provides a process for the production of 3',4'-dideoxykanamycin B from kanamycin B which comprises the consecutive steps of:

reacting kanamycin B with a sulfonic halide of the formula:

R³SO₂X wherein R³ represents lower alkyl, aryl or aralkyl group and X represents a halogen atom, in the presence of a base to produce a penta-N-sulfonylated kanamycin B of the formula:

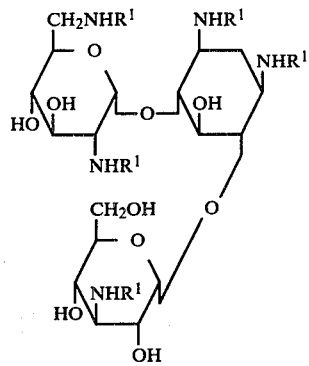

(V)

wherein each R¹ represents —SO₂R³ in which R³ is as defined above;

reacting the sulfonylated compound of the formula (V) with an alkylidenating, arylidenating, cyclohexylidenating or tetrahydropyranylidenating agent for protecting the 4''- and 6''-hydroxyl group to produce a compound of the formula:

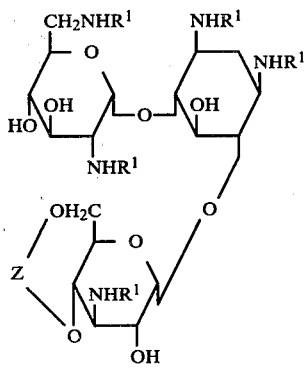

(VI)

wherein R¹ is as defined above and Z represents alkylidene, arylidene, cyclohexylidene or tetrahydropyranylidene group;

further reacting the compound of the formula (VI) with a sulfonic halide of the formula: R³SO₂X wherein R³ and X are as defined above provided that this sulfonic halide may be the same as or different from that used for the first sulfonylation, to produce a compound of the formula:

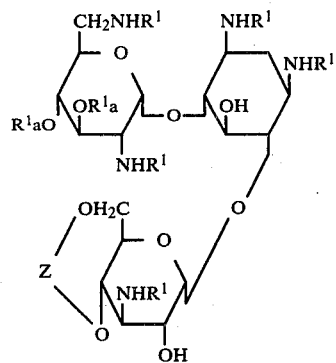

(VII)

wherein R¹ and Z are as defined above, R¹a has the same meaning as R¹ but may be the same as or different from R¹, and R² represents hydrogen atom or group R¹a;

treating the compound of the formula (VII) with a metal iodide to produce a 3',4'-unsaturated compound of the formula:

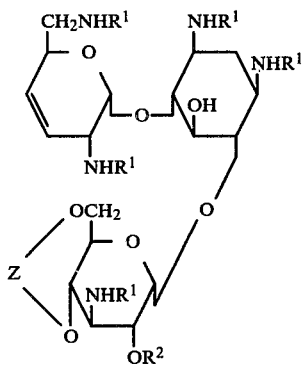

(VIII)

wherein R¹, Z and R² are as defined above;

subjecting the unsaturated compound of the formula (VIII) to hydrogenation to produce a compound of the formula:

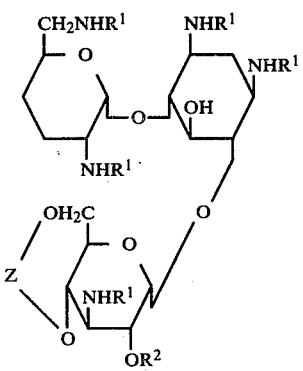

(IV)

wherein R¹, Z and R² are as defined above;

treating the compound of the formula (IV) in a manner known per se to remove the protecting radical Z, to produce a compound of the formula:

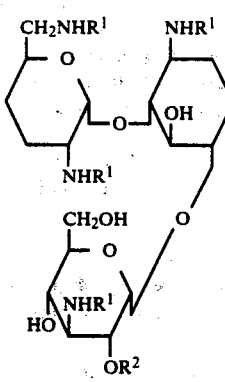

(II)

wherein R¹ and R² are as defined above; and interacting the compound of the formula (II) with an alkali or alkaline earth metal in ammonia or a lower alkylamine or a mixture thereof to remove all the protecting groups R¹ and R² and to produce 3',4'-dideoxykanamycin B.

With respect to the above third aspect process of this invention, it is possible, if desired, that the 3',4'-unsaturated compound of the formula (VIII) is at first treated in a manner known per se to remove the hydroxyl-protecting group Z, and the compound so obtained is interacted with an alkali or alkaline earth metal in ammonia, a lower alkylamine, a mixture thereof to remove the protecting radicals R¹ and R², followed by catalytic hydrogenation, to produce 3',4'-dideoxykanamycin B.

PREFERRED EMBODIMENT OF THE INVENTION

This invention is further illustrated but not limited by the following Examples.

EXAMPLE 1

(1) Penta-N-tosyl-kanamycin B

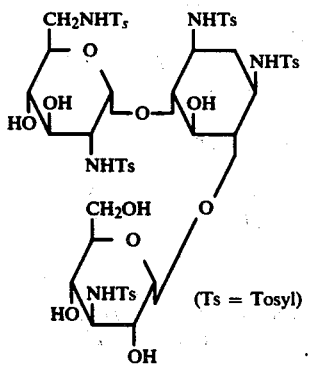

(Ts = Tosyl)

5.4 g of kanamycin B (free base) was dissolved in 55 ml. of water, to which was added 6.7 g of sodium carbonate followed by 110 ml. of dioxane. After ice-cooling 13 g of tosyl chloride (equivalent to approx. 6 moles per mole of kanamycin B) was added and the resultant mixture agitated for 10 hours under ice-cooling. The reaction solution was then concentrated under reduced pressure at nearly 45° C. and the concentrate poured into water. The suspension thus formed was filtered, washed with water until it was neutral and then with ether and dried to give 13.8 g of the crude product. The product was purified by column chromatography on silica gel eluting with chloroform-ethanol (10:1) to give 10.2 g (73%) of the title compound.

(2) Penta-N-tosyl-4",6"-O-cyclohexylidene kanamycin B

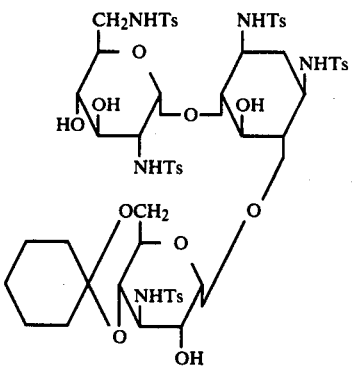

170 g of Penta-N-tosyl-kanamycin B was dissolved in 17 ml. of dimethylformamide, to which were added 53 mg of thoroughly dry p-toluenesulfonic acid and 0.6 ml. of cyclohexanon dimethylketal. The mixture was maintained at 50° C. under a pressure of 30 mmHg for 30 minutes to bring it into reaction. A sample of the reaction mixture was tested by thin layer chromatography on silica gel developed with ethyl acetatebenzene (3:1).

When there are shown disappearance of the spot of Rf=0.04 and formation of the spots of Rf=0.38 (attributable to the object compound) and of Rf=0.56 (attributable to the dicyclohexylidene product) at a ratio of 2:1, then 0.01 ml. of water dissolved in dimethylformamide was added to the reaction mixture and the resultant mixture was allowed to stand at a ambient temperature overnight.

Subsequently, an aqueous saturated solution of 125 mg of sodium bicarbonate was added at once with thorough agitation and the solution obtained was concentrated under reduced pressure and then poured into water. The solid so formed was filtered off, washed with water and dried to give 1.80 g of the title compound. m.p. 175°–176° C. (decomp.). $[\alpha]_D^{25} = +13°$ (c=1 in DMF).

Analysis Calcd. for $C_{59}H_{75}N_5O_{20}S_5$: C 53.10; H 5.66; N 5.25; S 12.01%: Found: C 52.73; H 5.51; N 4.83; S 11.68%.

(3)
3',4'-Di-O-benzylsulfonyl-penta-N-tosyl-4",6"-O-cyclohexylidene kanamycin B and
3',4',2"-tri-O-benzylsulfonyl-penta-N-tosyl-4",6"-O-cyclohexylidene kanamycin B

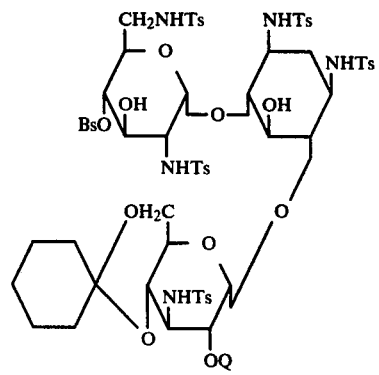

Q = H or Bs    Bs = SO₂CH₂— 

1.76 g of penta-N-tosyl-4",6"-O-cyclohexylidene kanamycin B was dissolved in 36 ml. of pyridine, to which was added 505 mg (2 molar proportion) of benzylsulfonyl chloride and the mixture was kept at a temperature of −3° to −5° C. for 2.5 hours. Thereafter, 253 mg of benzylsulfonyl chloride was further added and the resultant mixture was allowed to stand at about 3° C. overnight, followed by addition of 0.4 ml. of water. The reaction solution was concentrated to leave a dark red syrup, which was dissolved in 120 ml. of chloroform. The solution was washed successively with 10% potassium bisulfate solution, 5% aqueous sodium bicarbonate and water and dried over magnesium sulfate. The chloroform was distilled off to leave 2.16 g of a brown solid consisting essentially of a mixture of the title compounds.

This mixture was purified by passing it through a column of silica gel (Wacogel C-200, 140 g) using benzene-ethyl acetate (3:2) as the eluent to give 1.31 g (61%) of 3',4'-di-O-benzylsulfonyl-penta-N-tosyl-4",6"-O-cyclohexylidene kanamycin B having m.p. 169°–170° C. (decomp.) and $[\alpha]_D^{25} = 0°$ (c=1 in chloroform) and 473 mg (20%) of 3',4',2"-tri-O-benzylsulfonyl-penta-N-tosyl-4",6"-O-cyclohexylidene kanamycin B having m.p. 163°–164° C. (decomp.) and $[\alpha]_D^{25} = +20°$ (c=1 in chloroform). These two products could be used together, without separation as above, in the subsequent reaction step with the same results.

(4)
Penta-N-tosyl-4",6"-O-cyclohexylidene-3',4'-dideoxy-3'-enokanamycin B

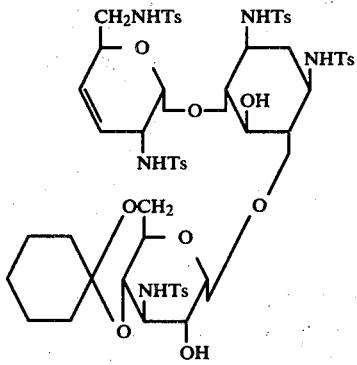

199 mg of 3',4'-di-O-benzylsulfonyl-penta-N-tosyl-4",6"-O-cyclohexylidene kanamycin B prepared as described in the procedure (3) was dissolved in 4 ml. of dimethylformamide, to which was added 2.03 g of dry sodium iodide and the mixture was maintained at 100° C. for 30 minutes with agitation. The reaction solution became homogeneous in two minutes and gradually changed from redish brown to dark brown due to formation of iodine. While the reaction solution remained hot, chloroform was added thereto and the precipitate was separated by filtration. The solid was well washed with chloroform and the washing was combined with the filtrate. The combined chloroform solution was concentrated under reduced pressure and the dimethylformamide associated with the chloroform was removed. The residue was taken up in chloroform and washed with 5% aqueous hypo solution to remove the iodine and further washed with water. The chloroform solution was then dried over anhydrous magnesium sulfate and the solvent distilled off to give 137 mg (87%) of the title compound.

Analysis Calcd. for C₅₉H₇₃N₅O₁₈S₅: C, 54.49; H, 5.66; N, 5.39; S, 12.33%: Found: C, 54.32; H, 5.51; N, 5.16; S, 11.97%.

(5)
2"-O-benzylsulfonyl-penta-N-tosyl-4",6"-O-cyclohexylidene-3',4'-dideoxy-3'-enokanamycin B

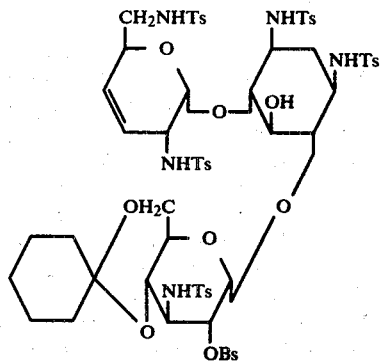

232 mg of 3',4',2"-tri-O-benzylsulfonyl-penta-N-tosyl-4",6"-O-cyclohexylidene kanamycin B was dissolved in 4.6 ml. of dimethylformamide, to which was added 2.44 g of sodium iodide and the mixture was maintained at 100° C. for one hour to cause the reaction. Thereafter, 20 ml. of chloroform was added followed by 5% aqueous hypo solution and the resultant mixture was thoroughly shaken. The chloroform layer was separated, washed with water, dried over magnesium sulfate and then concentrated. The dimethylformamide associated was removed by azeotropic distillation with toluene to leave 197 mg of a light brown solid. This solid was purified by the passage through a column of silica gel (Wacogel C-200, 10 g) using benzene-ethyl acetate (2:1) to give 164 mg (87%) of the title compound as colourless solid. m.p. 156°–157° C. (decomp.). $[\alpha]_D^{23} = -15°$ (c=1 in chloroform).

Analysis Calcd. for C₆₆H₇₉N₅O₂₀S₆: C, 54.49; H, 5.47; N, 4.81; S, 13.22%: Found: C, 54.17; H, 5.49; N, 4.50; S, 12.95%.

(6)
Penta-N-tosyl-4",6"-O-cyclohexylidene-3',4'-dideoxykanamycin B

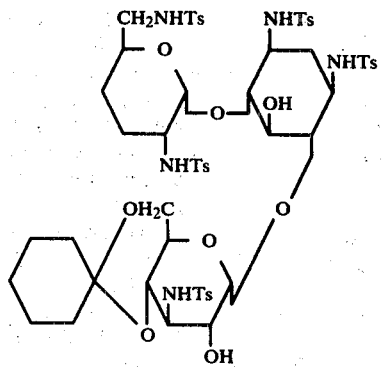

157 mg of penta-N-tosyl-4″,6″-O-cyclohexylidene-3′-enokanamycin B was dissolved in a mixture of 1.5 ml. or ethyl acetate and 0.5 ml. of dioxane. 30 mg of platinum oxide was added to the solution and the mixture maintained at ambient temperature under a hydrogen pressure of 3.5 atm. for one hour. To the reaction solution was added dioxane, which was heated to allow the dissolution, followed by filtration to remove the platinum. Concentration of the filtrate gave a syrup, to which was then added water. The precipitant thus formed was separated by centrifugation and dried to afford 124 mg (84%) of the title compound as white solid. m.p. 155°–156° C. $[\alpha]_D^{23} = 0°$ (c=0.4 in dimethylformamide).

Analysis Calcd. for $C_{59}H_{75}N_5O_{18}S_5$: C, 54.40; H, 5.80; N, 5.38; S, 12.31%: Found: C, 53.91; H, 5.79; N, 4.96; S, 11.74%.

(7) 2″-O-benzylsulfonyl-penta-N-tosyl-4″,6″-O-cyclohexylidene-3′,4′-dideoxykanamycin B

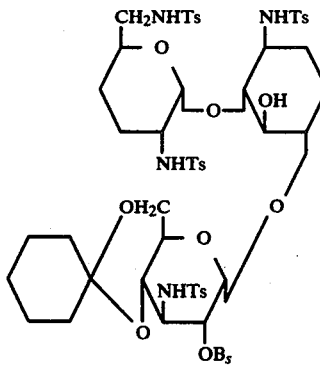

112 mg of 2′-O-benzylsulfonyl-penta-N-tosyl-4″,6″-O-cyclohexylidene-3′-enokanamycin B prepared as described in the above procedure (5) was dissolved in 2 ml. of dioxane, to which was added 30 mg of platinum oxide and the mixture kept at ambient temperature under hydrogen at 3.5 atm. for one hour. The catalyst was then removed by passing through a column of silica gel, followed by washing with dioxane. Removal of the dioxane by distillation gave 113 mg of the title compound as colourless solid. m.p. 156°–157° C. (decomp.). $[\alpha]_D^{22} = +16°$ (c=1 in chloroform).

Analysis Calcd. for $C_{66}H_{81}N_5O_{20}S_6$: C, 54.42; H, 5.60; N, 4.81; S, 13.20%: Found: C, 54.56; H, 5.57; N, 4.69; S, 13.01%.

(8) Penta-N-tosyl-3′,4′-dideoxykanamycin B

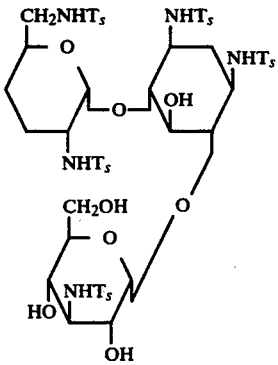

39.0 mg of penta-N-tosyl-4″,6″-O-cyclohexylidene-3′,4′-dideoxykanamycin B prepared as described in the above procedure (6) was suspended in a mixture of 1.1 ml. of acetic acid and 0.3 ml. of water and the suspension maintained at 80° C. for one hour. The reaction mixture took almost the state of a solution in about 10 minutes, and the insoluble matters was removed by filtration. The filtrate was concentrated and dried to give 31.0 mg (85%) of penta-N-tosyl-3′,4′-dideoxykanamycin B.

(9) 2″-benzylsulfonyl-penta-N-tosyl-3′,4′-dideoxykanamycin B

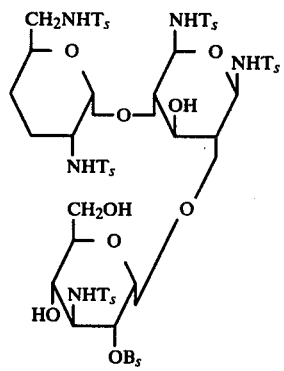

113 mg of 2″-O-benzylsulfonyl-penta-N-tosyl-4″,6″-O-cyclohexylidene-3′,4′-dideoxykanamycin B prepared as described in the procedure (7) was treated with 2 ml. of 80% acetic acid 80° C. for 1.5 hours. After the suspension was homogeneous, the reaction solution was concentrated under reduced pressure and subjected to azeotropic distillation with toluene to afford 104 mg (97%) of the title compound.

(10) Penta-N-tosyl-3′,4′-dideoxy-3′-enokanamycin B

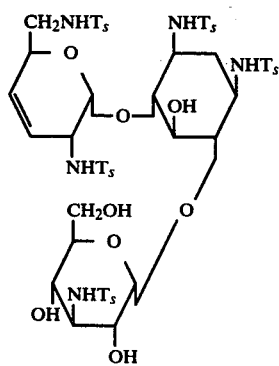

42 mg of penta-N-tosyl-4″,6″-O-cyclohexylidene-3′-enokanamycin B prepared as described in the procedure (4) was suspended in a mixture of 1 ml. of acetic acid and 0.3 ml. of water and the suspension maintained at 80° C. for one hour. After the reaction was completed, the insoluble matters were removed by filtration and the filtrate concentrated and dried to give 32 mg of the title compound.

(11)

2''-O-benzylsulfonyl-penta-N-tosyl-3',4'-dideoxy-3'-enokanamycin B

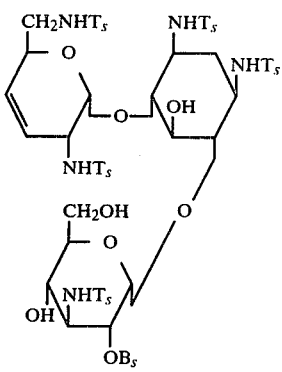

38 mg of 2''-O-benzylsulfonyl-penta-N-tosyl-4'',6''-O-cyclohexylidene-3',4'-dideoxy-3'-enokanamycin B prepared as described in the above procedure (5) was treated by the same procedure as indicated in the procedure (10) to give 27 mg of the title compound.

EXAMPLE 2

(1) 4'',6''-O-cyclohexylidene kanamycin B pentatosylate

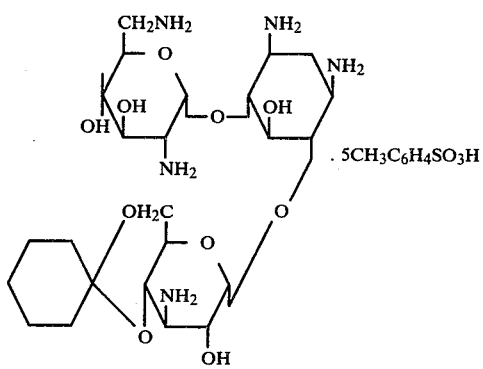

1.3 g of kanamycin B pentatosylate was dissolved in 25 ml. of dimethyl formamide, to which were added 450 mg of toluenesulfonic acid monohydrate and 0.7 ml. of cyclohexanone dimethyl ketal. The mixture was maintained at 50° C. and at 70 mmHg for 30 minutes, followed by addition of a great amount of ether to precipitate a solid. The solid was filtered off, well washed with ether and dried to give 1.15 g of the title compound.

(2)
Penta-N-benzylsulfonyl-3',4'-di-O-benzylsulfonyl-4'',6''-O-cyclohexylidene kanamycin B and
Penta-N-benzylsulfonyl-3',4',2''-tri-O-benzylsulfonyl-4'',6''-O-cyclohexylidene kanamycin B

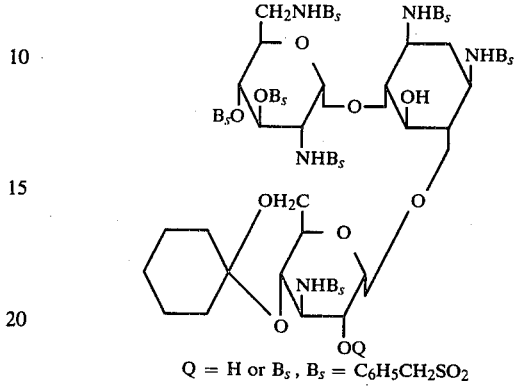

Q = H or $B_s$, $B_s$ = $C_6H_5CH_2SO_2$ 1.10 g of 4'',6''-O-cyclohexylidene kanamycin B pentatosylate was dissolved in 40 ml. of pyridine and the solution ice-cooled, followed by slow addition of 0.6 g of trimethylamine and 1.5 g of benzylsulfonyl chloride. The mixture was allowed to stand at about 3° C. overnight and 0.5 ml. of water added to the reaction solution, which was then concentrated to give a dark red syrup. The syrup was taken up in chloroform, washed successively with 10% potassium bisulfate solution, 5% aqueous sodium bicarbonate and water and dried over magnesium sulfate. Removal of the chloroform solvent left a solid, which was purified by means of a column of silica gel (Wacogel C-200) developed with benzeneethyl acetate (5:2) to yield 0.31 g of penta-N-benzylsulfonyl-3'-4'-di-O-benzylsulfonyl-4'',6''-O-cyclohexylidene kanamycin B having $[\alpha]_D^{25} = +5°$ (c=1 in chloroform) and 0.13 g of penta-N-benzylsulfonyl-3',4',2''-tri-O-benzylsulfonyl-4'',6''-O-cyclohexylidene kanamycin B having $[\alpha]_D^{25} = +18°$ (c=1 in chloroform).

(3)
Penta-N-benzylsulfonyl-4'',6''-O-cyclohexylidene-3',4'-dideoxy-3'-enokanamycin B

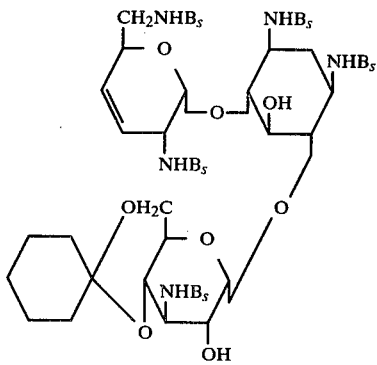

205 mg of penta-N-benzylsulfonyl-3',4'-di-O-benzylsulfonyl-4'',6''-O-cyclohexylidene kanamycin B was dissolved in 4 ml. of dimethylformamide, to which was added 2 g of sodium iodide and the mixture maintained at 100° C. for 30 minutes. Following the procedure as described in Example (1-4), there was obtained 145 mg of the title compound.

Analysis Calcd. for $C_{59}H_{73}N_5O_{18}S_5$: C, 54.39; H, 5.66; N, 5.39; S, 12.33%: Found: C, 53.91; H, 5.40; N, 5.07; S, 11.83%.

(4) Penta-N-benzylsulfonyl-3',4'-dideoxykanamycin B

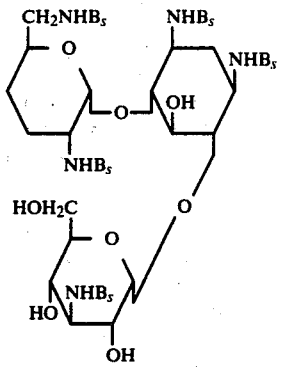

Penta-N-benzylsulfonyl-4",6"-O-cyclohexylidene-3',4'-dideoxy-3'-enokanamycin B was subjected to the same treatment as in Example (1-6) to effect the reduction of the 3',4'-double bond. The syrup substance thus formed was subjected, without purification, to the same treatment as in Example (1-8) to remove hydrolytically the cyclohexylidene radical, affording the title compound.

EXAMPLE 3

(1)
4",6"-O-cyclohexylidene-penta-N-mesyl-3',4',2"-tri-O-mesyl kanamycin B

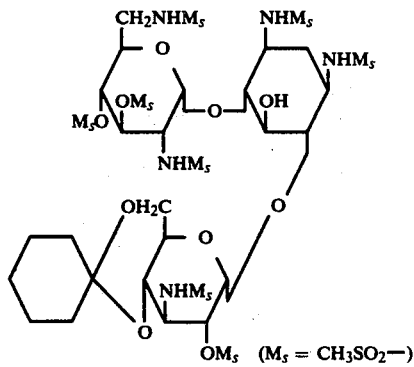

1.40 g of 4",6"-O-cyclohexylidene kanamycin B pentamesylate was dissolved in 40 ml. of pyridine and the solution ice-cooled, to which was added 0.7 g of triethylamine. The mixture was ice-cooled and 0.5 g of triethylamine further added thereto. The resultant mixture was allowed to stand overnight in a refrigerator, followed by addition of 0.5 ml. of water. The solution obtained was concentrated to give a syrup, which was taken up in chloroform, washed with water and dried over magnesium sulfate. Removal of the chloroform solvent left a solid and the latter was purified by a column of silica gel developed with chloroform to give 0.26 g of the title compound. $[\alpha]_D^{25} = +25°$ (c=1 in chloroform).

(2)
4",6"-O-cyclohexylidene-3',4'-dideoxy-3'-enopenta-N-mesyl-2"-O-mesyl kanamycin B

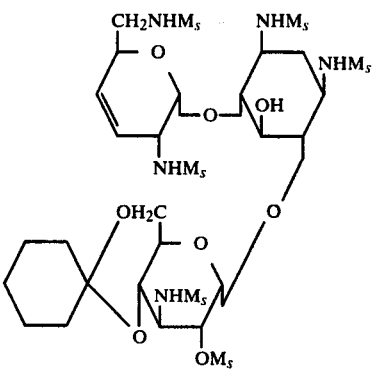

188 mg of 4",6"-O-cyclohexylidene-penta-N-mesyl-3',4',2"-tri-O-mesyl kanamycin B was dissolved in 4 ml. of dimethylformamide, to which was added 2 g of sodium iodide and the mixture maintained at 100° C. for 30 minutes.

The subsequent treatment carried out as in Example (1-4) gave 140 mg of the title compound.

Analysis Calcd. for $C_{30}H_{55}N_5O_{20}S_6$: C, 36.11; H, 5.56; N, 7.02; S, 19.24%: Found: C, 36.35; H, 5.71; N, 7.29; S, 18.80%.

(3) Penta-N-mesyl-2"-O-mesyl kanamycin B

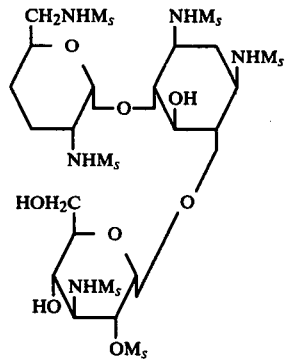

140 mg of 4",6"-O-cyclohexylidene-3',4'-dideoxy-3'-eno-penta-N-mesyl-2"-O-mesyl kanamycin B prepared as in the procedure (2) was dissolved in 5 ml. of a mixture of water-dioxane (1:4), to which was added platinum oxide, and the mixture obtained was maintained at ambient temperature under a hydrogen pressure of 3.5 atm. for one hour. Thereafter, the reaction solution was filtered and the filtrate concentrated to give a syrup, which was taken up in a mixture of water-acetic acid (1:3). The resultant solution was maintained at 80° C. for one hour and then concentrated to dryness to yield 107 mg of the title compound.

EXAMPLE 4

3',4'-Dideoxy-kanamycin B 26.3 mg of penta-N-tosyl-3',4'-dideoxykanamycin B prepared as in Example (1-8) was dissolved in 5 ml. of liquid ammonia at −60° C., to which was then added approx. 5 mg of sodium metal. About 15 minutes later the sodium was completely dissolved and the solution became pale yellow, followed by further addition of approx. 5 mg of sodium. After 30 minutes the reaction solution remained dark blue, showing the completion of the reaction. Then, ammonium chloride was added in small portions to make the solution yellow. The solution was slowly warmed to room temperature to remove ammonia and the residue taken up in water. The solution so obtained was neutralized with acetic acid and then placed in a column of CM-Sephadex C-25 (Pharmacia Co. Sweden). The column was washed with 30 ml. of water and then gradient-chromatographed with 0.03 to 0.3 N aqueous ammonia.

The eluate was collected in fractions, and the active fractions were combined together and concentrated to dryness to afford 10 mg of 3',4'-dideoxykanamycin B monocarbonate. The formation of the monocarbonate appeared to be owing to the absorption of carbon dioxide from the atmosphere.

This product showed Rf=0.19 in the thin-layer chromatography on silica gel using n-butanol/ethanol/chloroform/17% ammonia (4:4:2:3) as the eluent. The value Rf=0.19 was identical to that of authentic 3',4'-dideoxykanamycin B.

Antibacterial spectrum of said product was also identical to that of 3',4'-dideoxykanamycin B.

EXAMPLE 5

The procedure of Example 4 was repeated but starting from 21.9 mg of 2"-O-benzylsulfonyl-penta-N-tosyl-3',4'-dideoxykanamycin B prepared as in Example (1–9) which was dissolved in 2 ml. of liquid ammonia. There was then obtained 80 mg of 3',4'-dideoxykanamycin B monocarbonate as colourless solid, of which thin layer chromatogram and antibacterial spectrum were both identical to those of the anthentic sample.

EXAMPLE 6

32 mg of 2"-O-benzylsulfonyl-penta-N-tosyl-3',4'-dideoxykanamycin B was dissolved in a cooled mixture (about −30° C.) of 2.5 ml. of ethylamine and 3 ml. of liquid ammonia, to which was then added approx. 10 mg of sodium metal. The resultant mixture was slowly warmed with agitation to allow gradual dissolution of the sodium, whereby the reaction proceeded very mildly. After 3 hours the reaction solution was warmed to remove the solvent and the residue taken up in water. The solution was neutralized with p-toluenesulfonic acid and concentrated to dryness to give a solid, which was well dried and extracted three times with dimethylformamide at about 50° C. The combined extract was concentrated to dryness. The substantially desalted material thus obtained was placed in a column of CM-Sephadex C-25 which was then washed with water and gradient-chromatographed with 0.03 to 0.3 N aqueous ammonia. The eluate was collected in fractions, and the active fractions were combined together and concentrated to dryness to afford 11.5 mg of 3',4'-dideoxykanamycin B monocarbonate.

EXAMPLE 7

The procedure described in Example 6 was repeated except that 31.7 mg of 2"-O-benzylsulfonyl-penta-N-tosyl-3',4'-dideoxykanamycin B was dissolved in 4 ml. of ethylamine at 0° C., to which was then added about 10 mg of lithium metal. There was thus obtained 11 mg of 3',4'-dideoxykanamycin B monocarbonate.

EXAMPLE 8

Following the procedure described in Example 6 except that 31.3 mg of 2"-O-benzylsulfonyl-penta-N-tosyl-3',4'-dideoxykanamycin B was dissolved in 4 ml. of ethylamine at 0° C., followed by addition of about 10 mg of potassium metal, there was obtained 10.8 mg of 3',4'-dideoxykanamycin B monocarbonate.

EXAMPLE 9

(a) The same procedure as in Example 4 except starting from 25 mg of penta-N-benzylsulfonyl-3',4'-dideoxykanamycin B gave 8.5 mg of 3',4'-dideoxykanamycin B monocarbonate, which was found to be identical to authentic 3',4'-dideoxykanamycin B with respect to their thin-layer chromatogram and anti-bacterial spectrum.

(b) 1.53 g of the mixture of penta-N-benzylsulfonyl-3",4'-di-O-benzylsulfonyl-4",6"-O-cyclohexylidene kanamycin B and penta-N-benzylsulfonyl-3',4',2"-tri-O-benzylsulfonyl-4",6"-O-cyclohexylidene kanamycin B which was obtained prior to the separation by column chromatograph in the above Example (2—2) was subjected to the same treatment as in Example (2–3) and (4) to form 0.88 g of a mixture of penta-N-benzylsulfonyl-3',4'-dideoxykanamycin B and penta-N-benzylsulfonyl-2"-O-benzylsulfonyl-3',4'-dideoxykanamycin B.

The mixture was treated in the same manner as mentioned in the above procedure (b) to give 0.31 g of 3',4'-dideoxykanamycin B monocarbonate.

EXAMPLE 10

620 mg of the mixture of penta-N-benzylsulfonyl-3',4'-dideoxykanamycin B and penta-N-benzylsulfonyl-2"-O-benzylsulfonyl-3',4'-dideoxykanamycin B referred to in Example 9 was dissolved in 30 ml. of ethylamine, to which was slowly added lithium metal. The subsequent treatment carried out as in Example 7 gave 229 mg of 3',4'-dideoxykanamycin monocarbonate.

EXAMPLE 11

Following the same procedure as in Example 4 except that 27.7 mg of penta-N-mesyl-2"-O-mesyl kanamycin B prepared as described in Example (3—3) was dissolved in 5 ml. of liquid ammonia at −60° C., there was obtained 13.7 mg of 3',4'-dideoxykanamycin B monocarbonate which was found to be identical to the authentic 3',4'-dideoxykanamycin B with respect to their thin-layer chromatogram and antibacterial spectrum.

EXAMPLE 12

(1) 26 mg of penta-N-tosyl-3',4'-dideoxy-3'-enokanamycin B prepared as described in Example (1–10) was dissolved in 4 ml. of ethylamine at 0° C., to which was added about 5 mg of lithium metal and the mixture was maintained at this temperature for 3 hours. The subsequent treatment following Example 7 gave 9.6 mg of 3',4'-dideoxy-3'-enokanamycin B monocarbonate.

(2) 11.0 mg of 3',4'-dideoxy-3'-enokanamycin B monocarbonate prepared as above was dissolved in 0.5 ml. of water, to which was added one drop of acetic acid followed by 2 mg of platinum oxide. The mixture was agitated at ambient temperature for one hour under a hydrogen atmosphere at a pressure of 3.5 atm. The reaction solution was then filtered and the filtrate concentrated to give a solid, which was placed in a column of CM-Sephadex C-25. The column was washed with water and gradient-chromatographed with 0.03 to 0.3 N aqueous ammonia. The eluate was collected in fractions, and the active fractions were combined together and concentrated to dryness. There was obtained 9.8 mg of 3',4'-dideoxykanamycin B monocarbonate which was found to be identical to the authentic 3',4'-dideoxykanamycin B monocarbonate with respect to their thin layer chromatogram and antibacterial spectrum.

What we claim is:

1. A compound of the formula

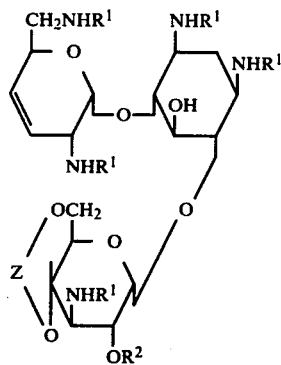

wherein $R^1$ is lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl, $R^2$ is hydrogen, lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl, and Z is lower alkylidene, arylidene formed from benzaldehyde, anisaldehyde or tolualdehyde, cyclohexylidene or tetrahydropyranylidene.

2. Penta-N-tosyl-4",6"-O-cyclohexylidene-3',4'-dideoxy-3'-enokanamycin B.

3. 2"-O-Benzylsulfonyl-penta-N-tosyl-4",6"-O-cyclohexylidene-3',4'-dideoxy-3'-enokanamycin B.

4. 4",6"-O-Cyclohexylidene-3',4'-dideoxy-3'-eno-penta-N-mesyl-2"-O-mesylkanamycin B.

5. Penta-N-tosyl-3',4'-dideoxy-3'-enokanamycin B.

6. A compound of the formula

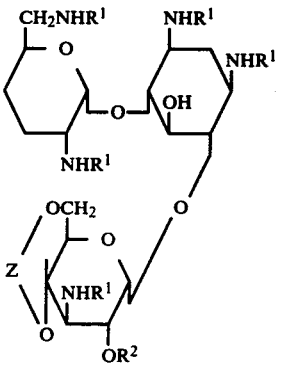

wherein $R^1$ is lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl, $R^2$ is hydrogen, lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl, and Z is lower alkylidene, arylidene formed from benzaldehyde, anisaldehyde or tolualdehyde, cyclohexylidene or tetrahydropyranylidene.

7. Penta-N-tosyl-4",6"-O-cyclohexylidene-3',4'-dideoxykanamycin B.

8. 2"-O-Benzylsulfonyl-penta-N-tosyl-4",6"-O-cyclohexylidene-3',4'-dideoxykanamycin B.

9. Penta-N-mesyl-2"-O-mesyl-4",6"-O-cyclohexylidene-3',4'-dideoxykanamycin B.

10. A compound of the formula

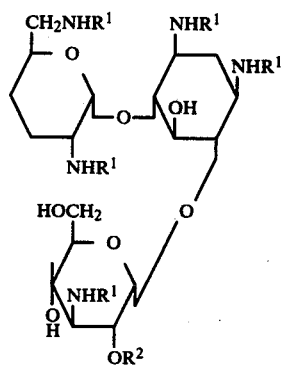

wherein $R^1$ is lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl and $R^2$ is hydrogen, lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl.

11. Penta-N-tosyl-3',4'-dideoxykanamycin B.

12. 2"-O-Benzylsulfonyl-3',4'-dideoxypenta-N-tosylkanamycin B.

13. 3',4'-Dideoxy-2"-O-methanesulfonyl-penta-N-tosylkanamycin B.

14. A compound of the formula

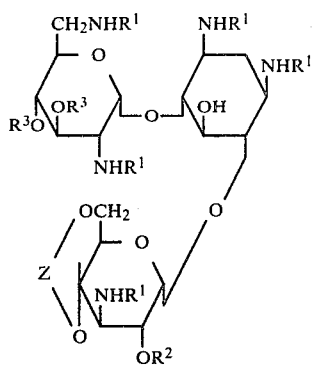

wherein $R^1$ is lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl, $R^2$ is hydrogen, lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl, Z is lower alkylidene, arylidene formed from benzaldehyde, anisaldehyde or tolualdehyde, cyclohexylidene or tetrahydropyranylidene, and $R^3$ is lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl.

15. 3′,4′-Di-O-benzylsulfonyl-4″,6″-O-cyclohexylidene-N-tosylkanamycin B.

16. 3′,4′,2″-Tri-O-benzylsulfonyl-4″,6″-O-cyclohexylidene-N-tosylkanamycin B.

17. 3′,4′-Di-O-benzylsulfonyl-4″,6″-O-cyclohexylidene-2″-O-methanesulfonyl-penta-N-tosylkanamycin B.

18. 4″,6″-O-Cyclohexylidene-3′,4′,2‴-tri-O-methanesulfonyl-penta-N-tosylkanamycin B.

19. A process which comprises reacting a compound of the formula

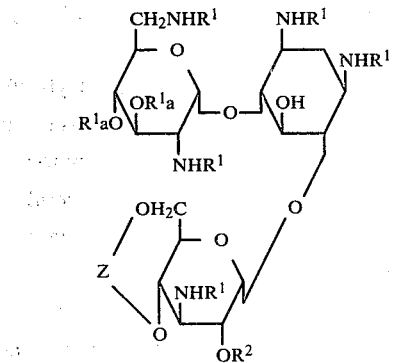

wherein $R^1$ is lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl, $R^2$ is hydrogen, lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl, Z is lower alkylidene, arylidene formed from benzaldehyde, anisaldehyde or tolualdehyde, cyclohexylidene or tetrahydropyranylidene, and $R^1a$ has the same meaning as $R^1$ but may be the same as or different from $R^1$ with sodium iodide in the absence of zinc dust to produce a 3′,4′-unsaturated compound of the formula

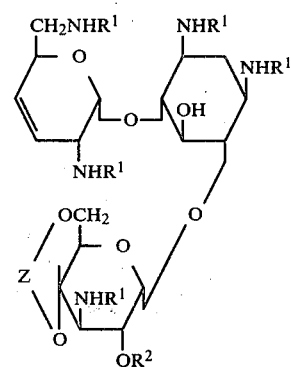

wherein $R^1$, Z and $R^2$ are as defined above.

20. A process which comprises reacting a compound of the formula

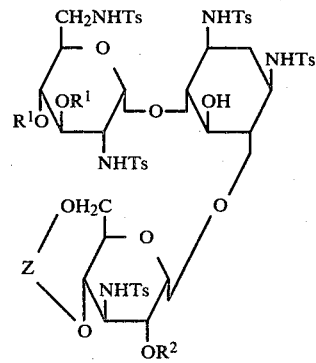

wherein Ts is p-toluenesulfonyl, $R^1$ is benzenesulfonyl, $R^2$ is hydrogen, lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl, and Z is lower alkylidene, arylidene formed from benzaldehyde, anisaldehyde or tolualdehyde, cyclohexylidene or tetrahydropyranylidene with sodium iodide in N,N-dimethylformamide in the absence of zinc dust to produce a 3′,4′-unsaturated compound of the formula

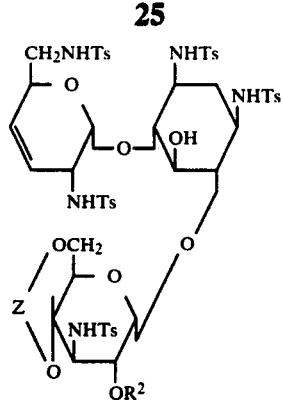
wherein Ts, Z and R² are as defined above.
* * * * *